(12) United States Patent
Takeshima

(10) Patent No.: US 11,619,694 B2
(45) Date of Patent: Apr. 4, 2023

(54) MAGNETIC RESONANCE IMAGING APPARATUS AND MEDICAL DATA PROCESSING APPARATUS

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

(*) Notice: Subject to any disclaimer, the term of this patent is extended or adjusted under 35 U.S.C. 154(b) by 0 days.

(21) Appl. No.: 17/446,628

(22) Filed: Sep. 1, 2021

(65) Prior Publication Data

US 2022/0065963 A1 Mar. 3, 2022

(30) Foreign Application Priority Data

Sep. 1, 2020 (JP) .............................. JP2020-146744
Aug. 30, 2021 (JP) .............................. JP2021-140258

(51) Int. Cl.
*G01R 33/48* (2006.01)
*G01R 33/56* (2006.01)
(Continued)

(52) U.S. Cl.
CPC .......... *G01R 33/4828* (2013.01); *A61B 5/055* (2013.01); *G01R 33/485* (2013.01); *G01R 33/543* (2013.01); *G01R 33/5608* (2013.01); *G06T 7/0012* (2013.01); *G06T 2207/10088* (2013.01); *G06T 2207/20081* (2013.01)

(58) Field of Classification Search
CPC .............. G01R 33/4828; G01R 33/485; G01R 33/543; G01R 33/5608; G01R 33/5602; G01R 33/5605; G01R 33/5607; G01R 33/56341; G01R 33/5635; A61B 5/055; (Continued)

(56) References Cited

U.S. PATENT DOCUMENTS

2010/0169024 A1  7/2010  Madabhushi et al.
2011/0218253 A1  9/2011  Lange et al.

FOREIGN PATENT DOCUMENTS

JP  2019111322 A  *  7/2019  ............. A61B 5/055

OTHER PUBLICATIONS

Qi et al., "A quantitative SVM approach potentially improves the accuracy of magnetic resonance spectroscopy in the preoperative evaluation of the grades of diffuse gliomas", NeuroImage: Clinical 23, 101835, 2019, 8 pages.
(Continued)

*Primary Examiner* — Susan S Lee
(74) *Attorney, Agent, or Firm* — Oblon, McClelland, Maier & Neustadt, L.L.P.

(57) ABSTRACT

A magnetic resonance imaging apparatus according to one embodiment includes sequence control circuitry and processing circuitry. The sequence control circuitry performs a first data acquisition for chemical shift measurement and a second data acquisition for either chemical shift measurement or MR imaging, which differs from chemical shift measurement, on the same subject under certain conditions that differ between those data acquisitions. The processing circuitry performs medical data classification on the subject based on first MR data obtained through the first data acquisition and second MR data obtained through the second data acquisition.

16 Claims, 9 Drawing Sheets

(51) Int. Cl.
*G01R 33/485* (2006.01)
*A61B 5/055* (2006.01)
*G06T 7/00* (2017.01)
*G01R 33/54* (2006.01)

(58) Field of Classification Search
CPC ......... G06T 7/0012; G06T 2207/10088; G06T 2207/20081
See application file for complete search history.

(56) References Cited

OTHER PUBLICATIONS

Akkus et al., "Predicting 1p19q Chromosomal Deletion of Low-Grade Gliomas from MR Images using Deep Learning" 2017, 7 pages, https://arxiv.org/RR/arxiv/papers/1611/1611.06939.pdf.

Scheau et al., "Magnetic Resonance Spectroscopy—a non-invasive method in evaluating focal and diffuse central nervous system disease" Journal of Medicine and Life, vol. 5, issue 4, Oct.-Dec. 2012, pp. 423-427.

Lazovic et al., "Detection of 2-hydroxyglutaric acid in vivo by proton magnetic resonance spectroscopy in U87 glioma cells overexpressing isocitrate dehydrogenase-1 mutation", Neuro-Oncology 14 (12), 2012, pp. 1465-1472.

\* cited by examiner

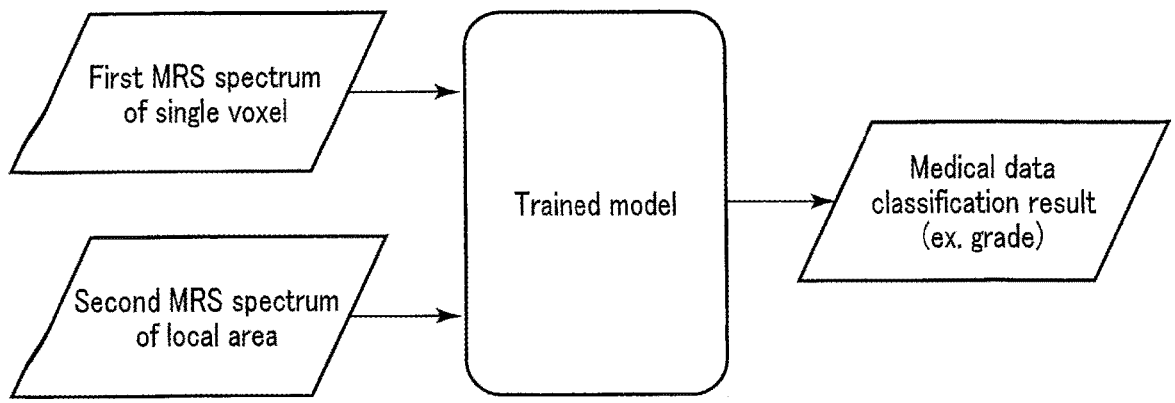
F I G. 9
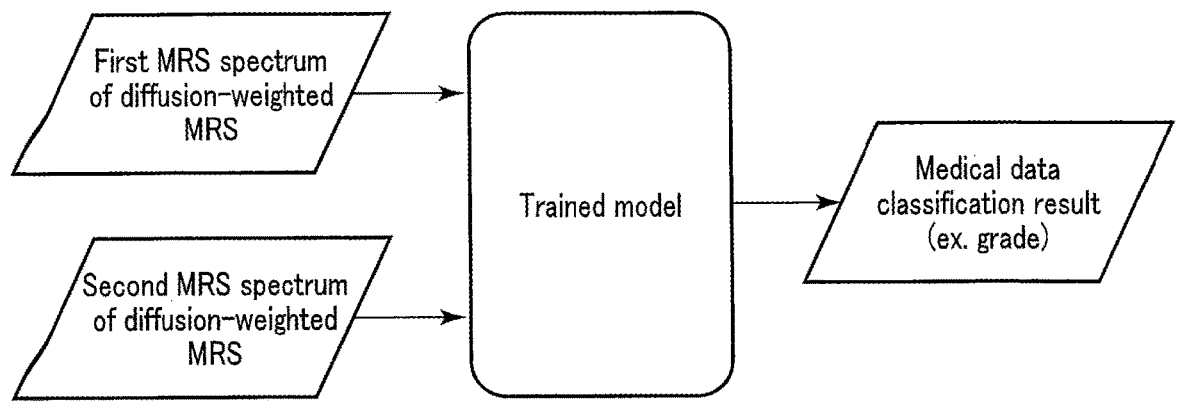
F I G. 10
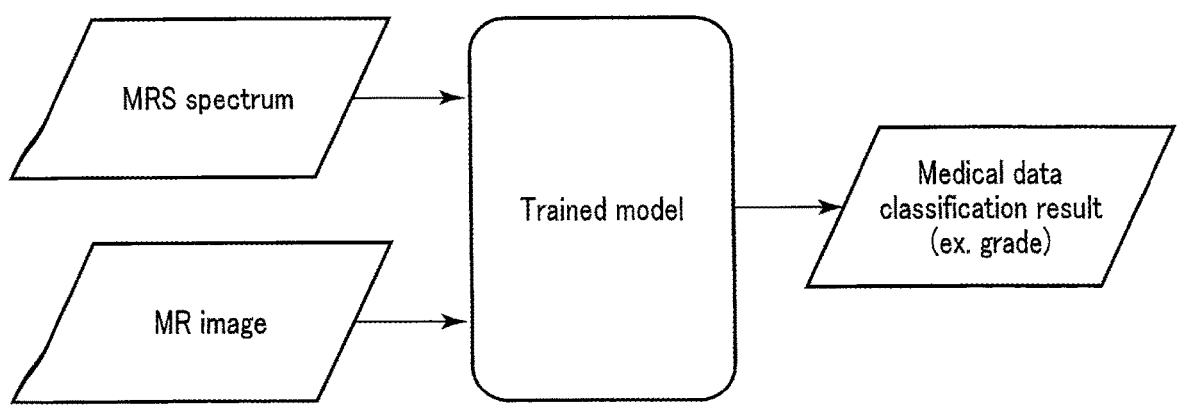
F I G. 11

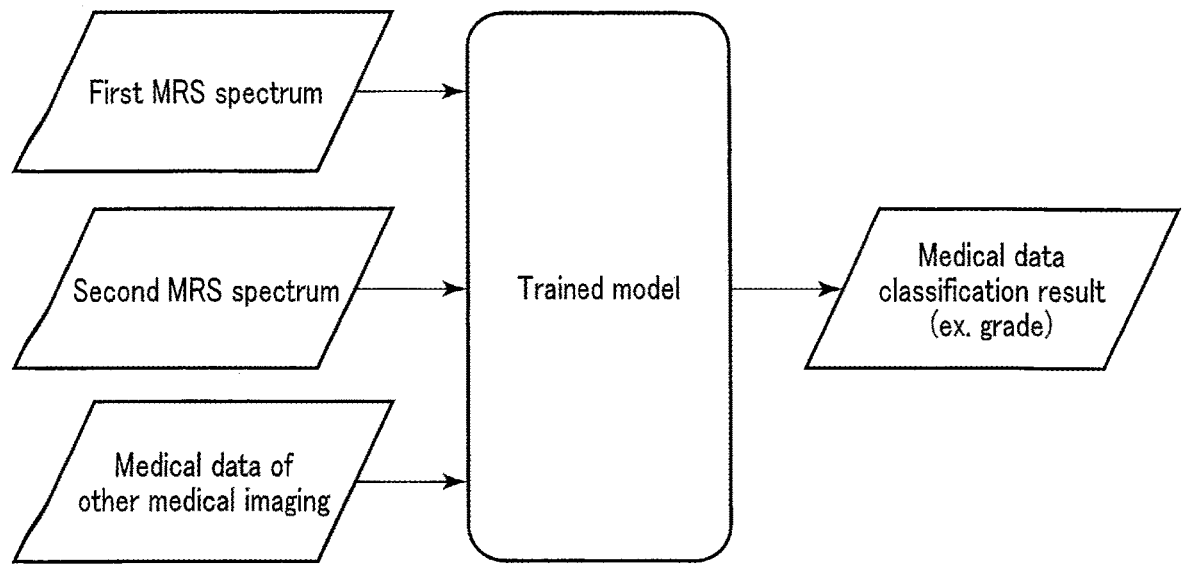
F I G. 12
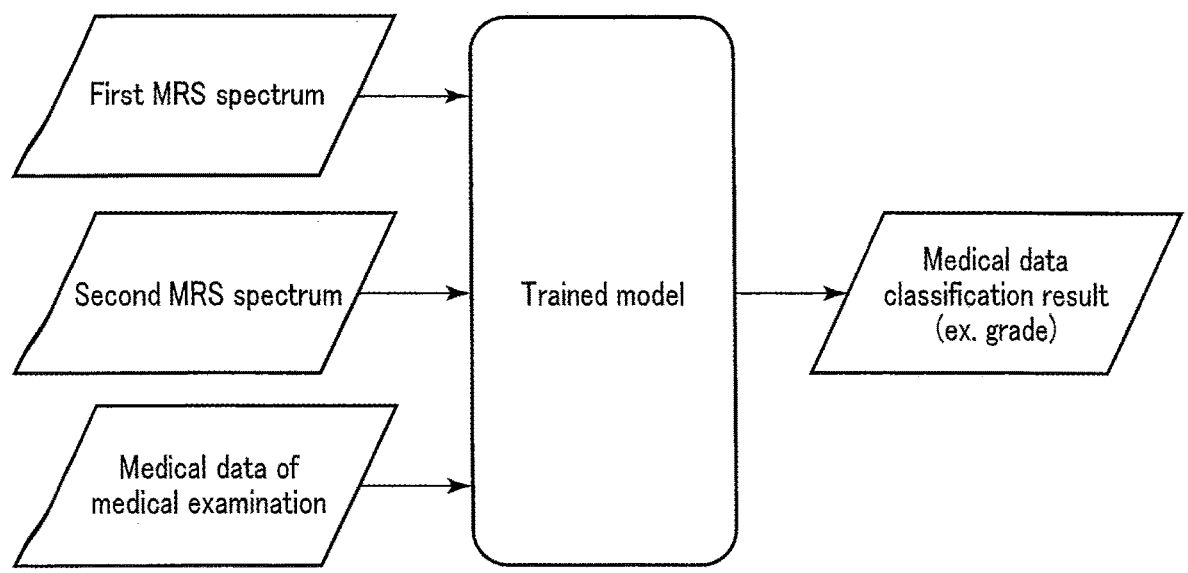
F I G. 13

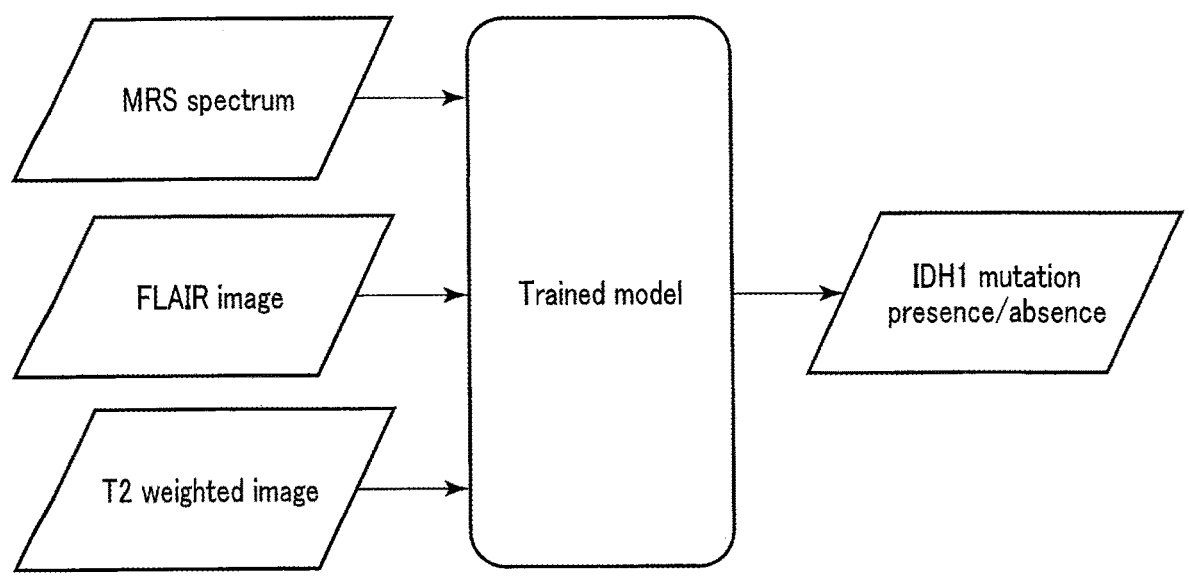
F I G. 14

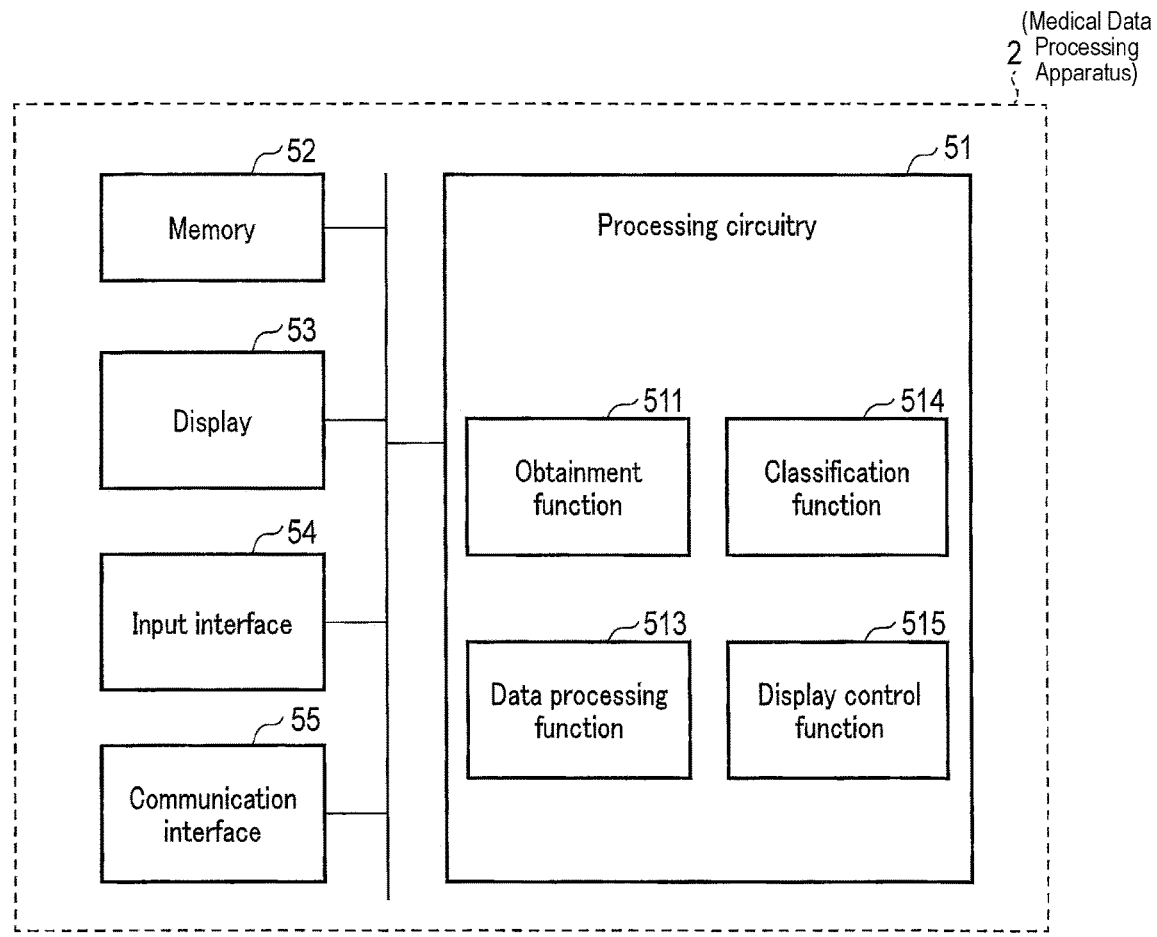
F I G. 15
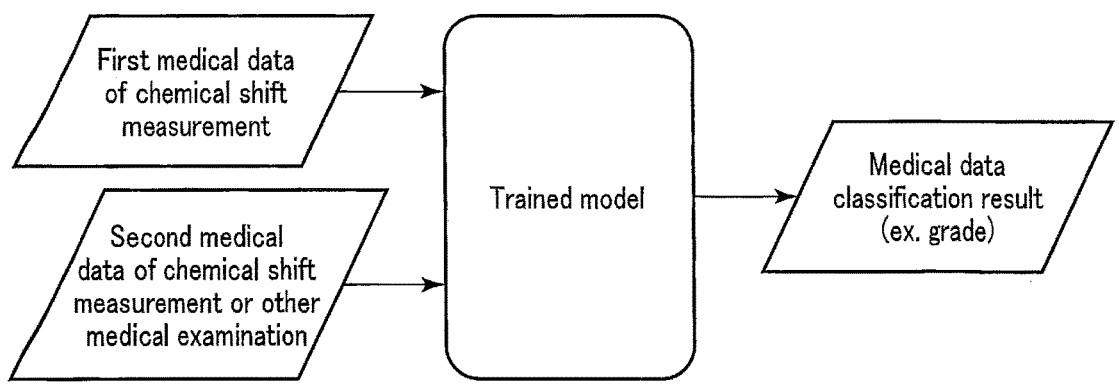
F I G. 16

MAGNETIC RESONANCE IMAGING APPARATUS AND MEDICAL DATA PROCESSING APPARATUS

CROSS-REFERENCE TO RELATED APPLICATIONS

This application is based upon and claims the benefit of priority from Japanese Patent Application No. 2020-146744, filed Sep. 1, 2020, and No. 2021-140258, filed Aug. 30, 2021, the entire contents of all of which are incorporated herein by reference.

FIELD

Embodiments described herein relate generally to a magnetic resonance imaging apparatus and a medical data processing apparatus.

BACKGROUND

Techniques relating to grading using MR spectroscopy and grading using MR imaging are known. MR spectroscopy is an example of a method for measuring chemical shift, which is a slight difference in resonance frequencies caused by different chemical environments, and it is known that data acquisition by this MR spectroscopy method is unstable. Therefore, there is a demand for improving the accuracy of grading using MR spectroscopy.

BRIEF DESCRIPTION OF THE DRAWINGS

FIG. 9 is a diagram schematically showing an example of an input/output relationship of a trained model according to Example 4 of the first embodiment.

FIG. 10 is a diagram schematically showing an example of an input/output relationship of a trained model according to Example 5 of the first embodiment.

FIG. 11 is a diagram schematically showing an example of an input/output relationship of a trained model according to Example 6 of the first embodiment.

FIG. 12 is a diagram schematically showing an example of an input/output relationship of a trained model according to Example 7 of the first embodiment.

FIG. 13 is a diagram schematically showing an example of an input/output relationship of a trained model according to Example 8 of the first embodiment.

FIG. 14 is a diagram schematically showing an example of an input/output relationship of a trained model according to Example 10 of the first embodiment.

FIG. 15 is a diagram showing a configuration example of a medical data processing apparatus according to a second embodiment.

FIG. 16 is a diagram schematically showing an example of an input/output relationship of a trained model according to the second embodiment.

DETAILED DESCRIPTION

In general, according to one embodiment, a magnetic resonance imaging apparatus according to the present embodiment includes sequence control circuitry and processing circuitry. The sequence control circuitry performs a first data acquisition for chemical shift measurement and a second data acquisition for either chemical shift measurement or MR imaging, which differs from chemical shift measurement, on the same subject under certain conditions that differ between those data acquisitions. The processing circuitry performs medical data classification on the subject based on first MR data obtained through the first data acquisition and second MR data obtained through the second data acquisition.

Hereinafter, embodiments of a magnetic resonance imaging apparatus and a medical data processing apparatus will be described in detail with reference to the drawings.

First Embodiment

Figure 1:
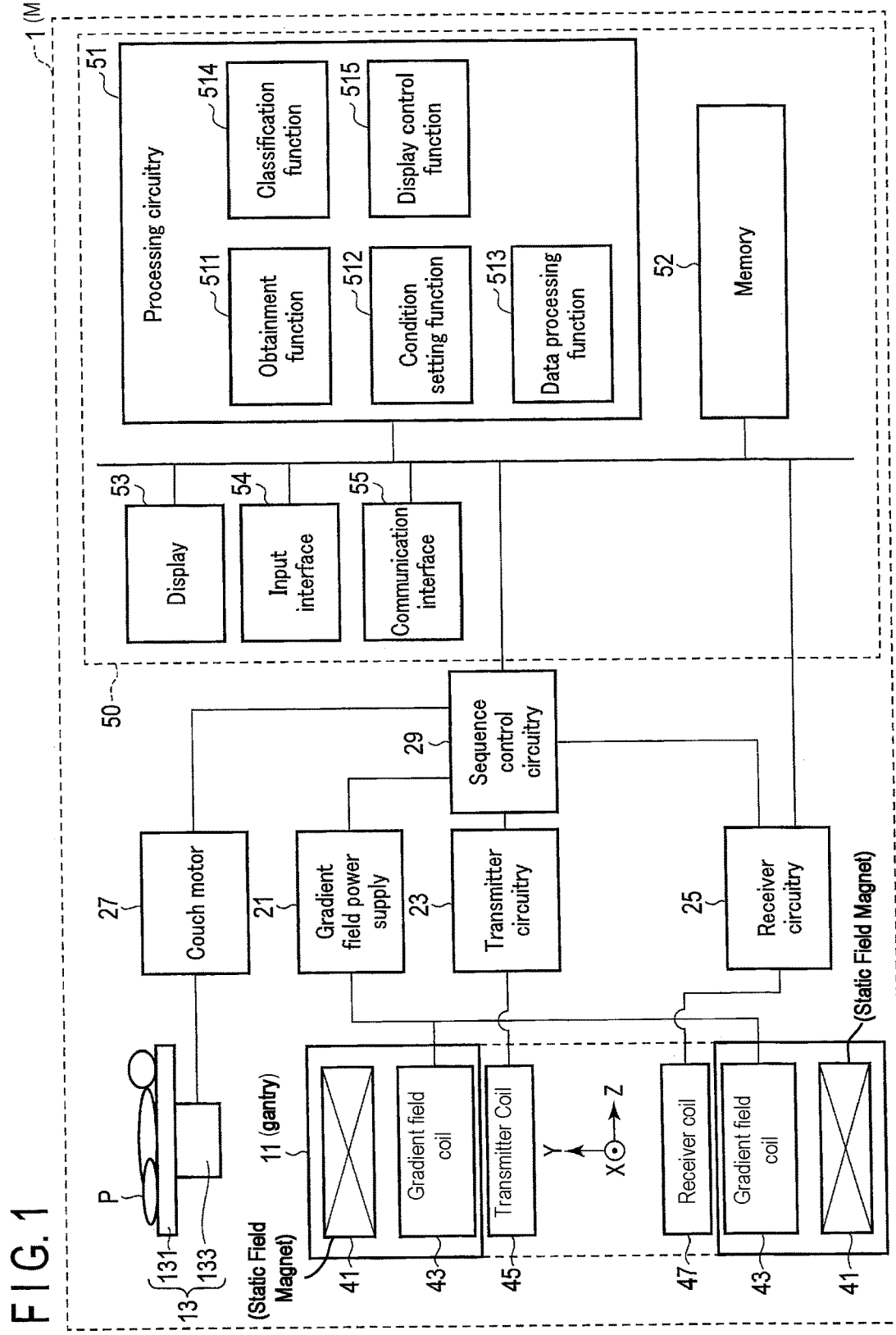
FIG. 1 is a diagram showing a configuration example of a magnetic resonance imaging apparatus according to a first embodiment.

FIG. 1 is a diagram showing a configuration example of a magnetic resonance imaging apparatus according to a first embodiment. As shown in FIG. 1, the magnetic resonance imaging (MRI) apparatus 1 includes a gantry 11, a couch 13, a gradient field power supply 21, transmitter circuitry 23, receiver circuitry 25, a couch motor 27, sequence control circuitry 29, and a host computer 50.

The gantry 11 includes a static field magnet 41 and a gradient field coil 43. The static field magnet 41 and the gradient field coil 43 are accommodated in the housing of the gantry 11. A bore with a hollow shape is formed in the housing of the gantry 11. A transmitter coil 45 and a receiver coil 47 are arranged in the bore of the gantry 11.

The static field magnet 41 has a hollow and essentially cylindrical shape, and generates a static magnetic field inside thereof. The static field magnet 41 uses, for example, a permanent magnet, a superconducting magnet, a normal conducting magnet, etc. The central axis of the static field magnet 41 is defined as a Z axis; an axis vertically perpendicular to the Z axis is defined as a Y axis; and an axis horizontally perpendicular to the Z axis is defined as an X axis. The X, Y, and Z axes constitute a three-dimensional orthogonal coordinate system.

The gradient field coil 43 is a coil unit mounted inside the static field magnet 41, and formed in a hollow and essentially cylindrical shape. The gradient field coil 43 generates a gradient field upon receiving a current supplied from the gradient field power supply 21. Specifically, the gradient field coil 43 includes three coils corresponding respectively to the X, Y, and Z axes which are perpendicular to each other. The three coils generate gradient fields in which the magnetic field magnitude changes along the X, Y, and Z axes. The gradient magnetic fields along the X, Y, and Z axes are combined to generate a slice selective gradient field Gs, a phase encode gradient field Gp, and a frequency encode gradient field Gr, which are perpendicular to each other, in desired directions. The slice selective gradient magnetic field Gs is used to discretionarily determine an imaging slice. The phase encoding gradient magnetic field Gp is used to change a phase of magnetic resonance signals (hereinafter "MR signals") in accordance with a spatial position. The frequency encoding gradient magnetic field Gr is used to change a frequency of MR signals in accordance with a spatial position. In the following description, it is assumed that the gradient direction of the slice selective gradient magnetic field Gs aligns with the Z axis, the gradient direction of the phase encoding gradient magnetic field Gp aligns with the Y axis, and the gradient direction of the frequency encoding gradient field Gr aligns with the X axis.

The gradient field power supply 21 supplies a current to the gradient field coil 43, in accordance with a sequence control signal from the sequence control circuitry 29. The gradient field power supply 21 supplies a current to the gradient field coil 43 to allow the gradient field coil 43 to generate gradient fields in the X, Y, and Z axis directions. These gradient fields are superimposed on the static magnetic field formed by the static field magnet 41 and applied to the subject P.

The transmitter coil 45 is arranged inside the gradient field coil 43 and generates a high-frequency pulse (hereinafter referred to as an RF pulse) upon receiving a current supplied from the transmitter circuitry 23.

The transmitter circuitry 23 supplies a current to the transmitter coil 45 to apply an RF pulse to the subject P in order to electrically excite target protons in the subject P via the transmitter coil 45. The RF pulse vibrates at a resonance frequency specific to the target protons, and also electrically excites those target protons. An MR signal is generated from an electrically excited target proton and detected by the receiver coil 47. The transmitter coil 45 may be, for example, a whole body (WB) coil. The WB coil may be used as a transmitter/receiver coil.

The receiver coil 47 receives MR signals generated from the target protons in the subject P due to the effects of the RF pulse. The receiver coil 47 includes a plurality of receiver coil elements which can receive MR signals. The received MR signals are supplied to the receiver circuitry 25 by wiring or wirelessly. Although not shown in FIG. 1, the receiver coil 47 has a plurality of receiver channels arranged in parallel. Each receiver channel includes a receiver coil element which receives MR signals, an amplifier which amplifies the MR signals, etc. MR signals are given off by each receiver channel. The total number of receiver channels may be equal to, more than, or less than the number of receiver coil elements.

The receiver circuitry 25 receives the MR signals generated from electrically excited target protons via the receiver coil 47. The receiver circuitry 25 generates digital MR signals by processing the received MR signals. The digital MR signals may be expressed in k-space, which is defined by spatial frequencies. Thus, the digital MR signals are referred to as k-space data. The k-space data is an example of MR data. The k-space data is supplied to the host computer 50 either by wiring or wirelessly.

The aforementioned transmitter coil 45 and receiver coil 47 are merely examples. A transmitter/receiver coil which has a transmit function and a receive function may be used instead of the transmitter coil 45 and the receiver coil 47. Alternatively, the transmitter coil 45, the receiver coil 47, and the transmitter/receiver coil may be combined.

The couch 13 is placed adjacent to the gantry 11. The couch 13 includes a table top 131 and a base 133. The subject P is placed on the table top 131. The base 133 enables the table top 131 to be slid along each of the X, Y, and Z axes. The couch motor 27 is housed in the base 133. The couch motor 27 moves the table top 131 under the control of the sequence control circuitry 29. The couch motor 27 may include any type of motor such as a servo motor or stepping motor.

The sequence control circuitry 29 includes, as hardware resources, a processor such as a Central Processing Unit (CPU) or a Micro Processing Unit (MPU), and a type of memory such as Read Only Memory (ROM) and Random Access Memory (RAM). The sequence control circuitry 29 controls the gradient field power supply 21, the transmitter circuitry 23, and the receiver circuitry 25 synchronously based on data acquisition conditions set in the condition setting function 512 of the processing circuitry 51, and collect k-space data relating to a subject P. The sequence control circuitry 29 is an example of the sequence control unit.

The sequence control circuitry 29 according to the present embodiment performs data acquisition for chemical shift measurement. Chemical shift is a slight difference between resonance frequencies of a targeted proton, such as a hydrogen atomic nuclei etc., which is caused by different chemical environments. As a method of chemical shift measurement, MR spectroscopy, chemical shift imaging, chemical exchange spectroscopy (CEST), or Z-spectrum analysis providing proton environment data (ZAPPED) are known, and the present embodiment is applicable to any of these methods. The sequence control circuitry 29 is also capable of performing data acquisition for MR imaging. The MR imaging according to the present embodiment means a data acquisition method other than the chemical shift measurement mentioned above. As the MR imaging according to the present embodiment, T1 weighted imaging, T2 weighted imaging, T2* weighted imaging, MR angiography, diffusion weighted imaging, an inversion recovery method, etc. are applicable; however, any other imaging methods are also applicable.

The sequence control circuitry 29 according to the present embodiment performs a first data acquisition for chemical shift measurement and a second data acquisition for either chemical shift measurement or MR imaging differing from chemical shift measurement on the same subject P. The data acquisition conditions differ between the first data acquisition and the second data acquisition.

As shown in FIG. 1, the host computer 50 is a computer having a processing circuitry 51, a memory 52, a display 53, an input interface 54, and a communication interface 55. The processing circuitry 51 is an example of a processing unit; the memory 52 is an example of a storage unit; the display 53 is an example of the display unit; the input interface 54 is an example of an input unit; and the communication interface 55 is an example of a communication unit.

The processing circuitry 51 includes a processor such as a CPU, etc. as hardware resources. The processing circuitry 51 functions as the main unit of the MRI apparatus 1. For example, the processing circuitry 51 executes various types of programs to implement an obtainment function 511, a condition setting function 512, a data processing function 513, a classification function 514, and a display control function 515. The obtainment function 511 is an example of an acquisition unit; the condition setting function 512 is an example of a setting unit; the data processing function 513 is an example of a spectrum generation unit, an image reconstruction unit, or an image processing unit; the classification function 514 is an example of a classification unit; and the display controlling function 515 is an example of a display unit.

Via the obtainment function 511, the processing circuitry 51 acquires various types of data. For example, the processing circuitry 51 acquires k-space data acquired by the sequence control circuitry 29. The processing circuitry 51 may acquire k-space data directly from the sequence control circuitry 29 or the receiver circuitry 25, or k-space data temporarily stored in the memory 52.

Via the condition setting function 512, the processing circuitry 51 sets data acquisition conditions automatically or manually. Specifically, in the present embodiment, data acquisition conditions for a first data acquisition for chemical shift measurement and a second data acquisition for either chemical shift measurement or MR imaging that differs from chemical shift measurement are set. The processing circuitry 51 sets data acquisition conditions in such a manner that they differ between a first data acquisition and a second data acquisition.

Via the data processing function 513, the processing circuitry 51 performs data processing on k-space data obtained by the obtainment function 511 to generate various types of MR data. For example, the processing circuitry 51 generates a spectrum indicating an MR signal strength at each frequency based on the k-space data obtained through a data acquisition for chemical shift measurement. As another example, the processing circuitry 51 reconstructs various types of MR images based on k-space data obtained through a data acquisition for MR imaging. For example, the processing circuitry 51 may perform various types of image processing on an MR image. For example, the processing circuitry 51 performs image processing such as volume rendering, surface rendering, pixel value projection processing, Multi-Planer Reconstruction (MPR) processing, Curved MPR (CPR) processing, and the like. The processing circuitry 51 is capable of performing various types of image processing, such as area extraction, image recognition, image analysis, positioning, etc. Spectrums and MR images are examples of MR data.

Via the classification function 514, the processing circuitry 51 performs medical data classification on a subject P based on first MR data obtained through a first data acquisition and second MR data obtained through a second data acquisition.

In the display control function 515, the processing circuitry 51 displays various types of information on the display 53. For example, the processing circuitry 51 causes the display 53 to display, for example, a spectrum and an MR image generated by the data processing function 513, a medical data classification result generated by the classification function 514, and a setting screen relating to the setting of data acquisition conditions performed by the condition setting function 512.

The memory 52 is a storage apparatus such as a hard disk drive (HDD), a solid state drive (SSD), an integrated circuitry storage apparatus, or the like that stores various information. The memory 52 may be a drive apparatus or the like that reads and writes various information from and to a portable storage medium such as a CD-ROM drive, a DVD drive, a flash memory, and the like. For example, the memory 52 stores data acquisition conditions, k-space data, MR images, and control programs, etc.

The display 53 displays various types of information via the display control function 515. Examples of appropriate displays 53 that can be used include a CRT display, a liquid crystal display, an organic EL display, an LED display, a plasma display, or any other display known in the art.

The input interface 54 includes an input apparatus that receives various commands from the user. Examples of the input apparatus that can be used include a keyboard, a mouse, various switches, a touch screen, a touch pad, and the like. It should be noted that the input apparatus is not limited to those having physical operation parts such as the mouse and the keyboard. For example, the examples of input interface 54 also include electrical signal processing circuitry that receives an electrical signal corresponding to an input operation from an external input apparatus provided separately from the MRI apparatus 1, and outputs the received electrical signal to various types of circuitry. The input interface 54 may be a speech recognition device that converts audio signals acquired by a microphone into command signals.

The communication interface 55 is an interface connecting the magnetic resonance imaging apparatus 1 with a workstation, a picture archiving and communication system (PACS), a hospital information system (HIS), a radiology information system (RIS), and the like via a local area network (LAN) or the like. The network IF transmits and receives various information to and from the connected workstation, PACS, HIS and RIS.

It should be noted that the above configuration is merely an example, and the present embodiment is not limited thereto. For example, the sequence control circuitry 29 may be incorporated in the host computer 50. Also, the sequence control circuitry 29 and the processing circuitry 51 may be implemented on the same substrate. The condition setting function 512 is not necessarily implemented in the processing circuitry 51 of the MRI apparatus 1. For example, it suffices that the condition setting function 512 is implemented in a computer for setting data acquisition conditions, which is provided separate from the MRI apparatus 1. In this case, the data acquisition conditions generated by the computer are supplied to the MRI apparatus 1 via a network or a portable storage medium, etc. The storage area for the data acquisition conditions in the memory 52 is not necessarily implemented in the MRI apparatus 1 and may be implemented in a storage device connected to the MRI apparatus 1 via a network, for example.

Next, an example of the operation of the MRI apparatus 1 according to the present embodiment will be explained.

The processing circuitry 51 according to the present embodiment performs, via the classification function 514, medical data classification based on the first MR data and the second MR data. More specifically, the processing circuitry 51 applies the first MR data and the second MR data to a trained model and outputs a medical data classification result relating to a subject P.

Figure 2:
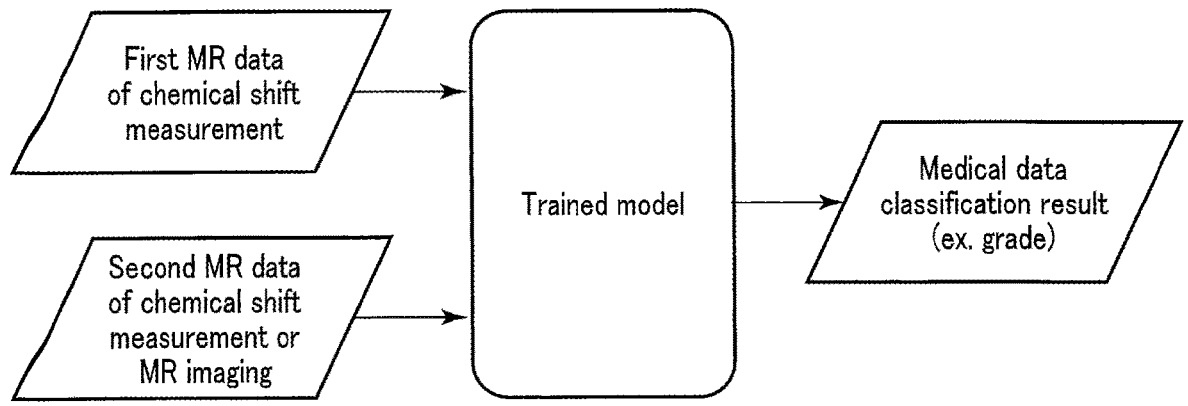
FIG. 2 is a diagram schematically showing an example of an input/output relationship of a trained model according to the first embodiment.

FIG. 2 is a diagram schematically showing an example of an input/output relationship of a trained model according to the first embodiment. As shown in FIG. 2, the trained model is a machine learning model into which first MR data of chemical shift measurement and second MR data of chemical shift measurement or MR imaging is input and in which parameters are learned so as to output a medical data classification result. As the trained model or the machine learning model according to the first embodiment, a classifier or an identifier, such as a neural network, deep neural network, support vector machine, or random forest, etc., is used. The medical data classification result is information indicating a result of medical data classification of first MR data and second MR data regarding a subject. As a medical data classification result, a grade of a disease by which a subject P is being affected is output, for example. As an output format, multiple classification is preferably but not restrictively used, with which a grade to which the subject P most likely belongs among multiple grades is output as a value close to "1" and a grade to which the subject P less likely belongs is output as a value close to "0". The output format is not limited to the above example, and a regression classification may be used in which a probability that the subject P belongs to a grade is expressed with a consecutive value for each grade. As a medical data classification result, a presence/absence or a probability of metastasis may be output.

The trained model according to the first embodiment may be generated by the MRI apparatus 1 or by another computer. Hereinafter, a computer having a processor such as a CPU or GPU, etc. for generating a trained model according to the first embodiment will be called a "model learning apparatus".

The model learning apparatus generates a trained model by having a machine learning model conduct machine learning based on multiple training samples. Training samples are combinations of first and second MR data as input data and a medical data classification result as correct answer data (hereinafter, "correct answer medical data classification result"). The first MR data and second MR data as input data are generated by the MRI apparatus 1 or other MRI apparatus. As the correct answer medical data classification result, a grade manually determined by medical staff by using the input data and medical information such as MR images, etc. relating to the same subject that the input data belongs to, is used. A grade may be determined by a computer in accordance with a predetermined algorithm based on the input data or medical information.

The model learning apparatus applies a machine learning model to the first MR data and the second MR data and performs a forward propagation process, and outputs a medical data classification result (hereinafter, "deducted medical data classification result"). Next, the model learning apparatus performs backpropagation by applying a difference (error) between the estimated classification result and the correct classification result to the machine learning model, and calculates a gradient vector, which is a derivative of an error function which is a parameter function. Subsequently, the model learning apparatus updates parameters of the machine learning model based on a gradient vector. These forward propagation processing, backpropagation processing, and parameter updating processing are repeated while changing the training samples, and a parameter that globally minimizes or locally minimizes an error function is determined in accordance with a predetermined optimization method. A trained model is generated by allocating the determined parameter to the machine learning model.

The first MR data is obtained through a first data acquisition and the second MR data is obtained through a second data acquisition, and different data acquisition conditions are set for the first data acquisition and the second data acquisition. By using the first MR data and the second MR data obtained under different data acquisition conditions, it is possible to perform medical data classification using more information than in the case where only the first data is used; it is thus possible to improve accuracy of the medical data classification.

Hereinafter, various examples of the MRI apparatus 1 according to the first embodiment are described. Although the chemical shift measurement is applicable to any of MR spectroscopy, chemical shift imaging, CEST, or ZAPPED in the following examples, assume that the chemical shift measurement is applied to MR spectroscopy as an example.

Example 1

In Example 1, assume MR spectroscopy, which is a type of chemical shift measurement, is used for both a first data acquisition and a second data acquisition. The MR spectroscopy is a data acquisition method for measuring a spectrum of a chemical shift. This spectrum is called an "MRS spectrum".

Figure 3:
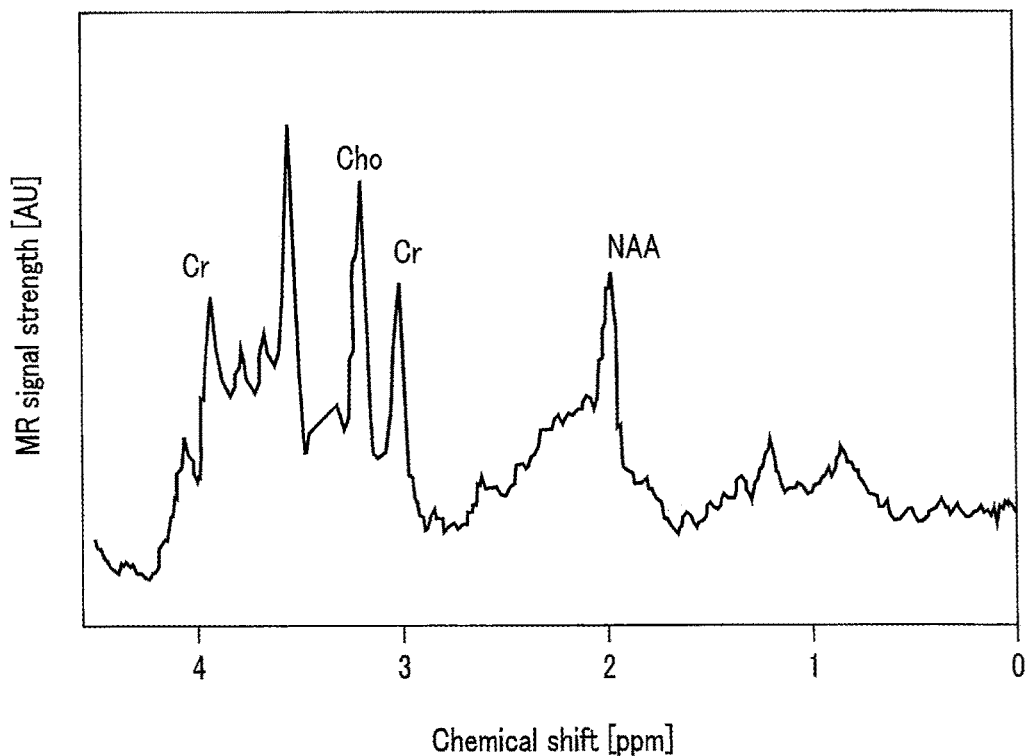
FIG. 3 is a drawing schematically showing an example of an MRS spectrum.

FIG. 3 is a drawing schematically showing an example of an MRS spectrum. The MRS spectrum shown in FIG. 3 is an example of an MRS spectrum of a subject's head. As shown in FIG. 3, in the MRS spectrum, the vertical axis defines an MR signal strength value [AU (arbitrary unit)] and the horizontal axis defines a difference from a reference frequency, namely chemical shift [ppm (parts per million)]. The reference frequency is set to a frequency of a discretionarily selected reference substance. Although not limited to a particular one, a reference substance is set to tetramethylsilane (TMS) for example. According to the MRS spectrum, it is possible to visualize an amount of metabolite, such as N-acetylaspartic acid (NAA), creatine (Cr), choline (Cho), etc., that is present.

Next, medical data classification processing by the MRI apparatus 1 according to Example 1 of the first embodiment will be described with reference to FIG. 4. In the following, assume the medical data classification is grading of a head tumor as a clinical example.

Figure 4:
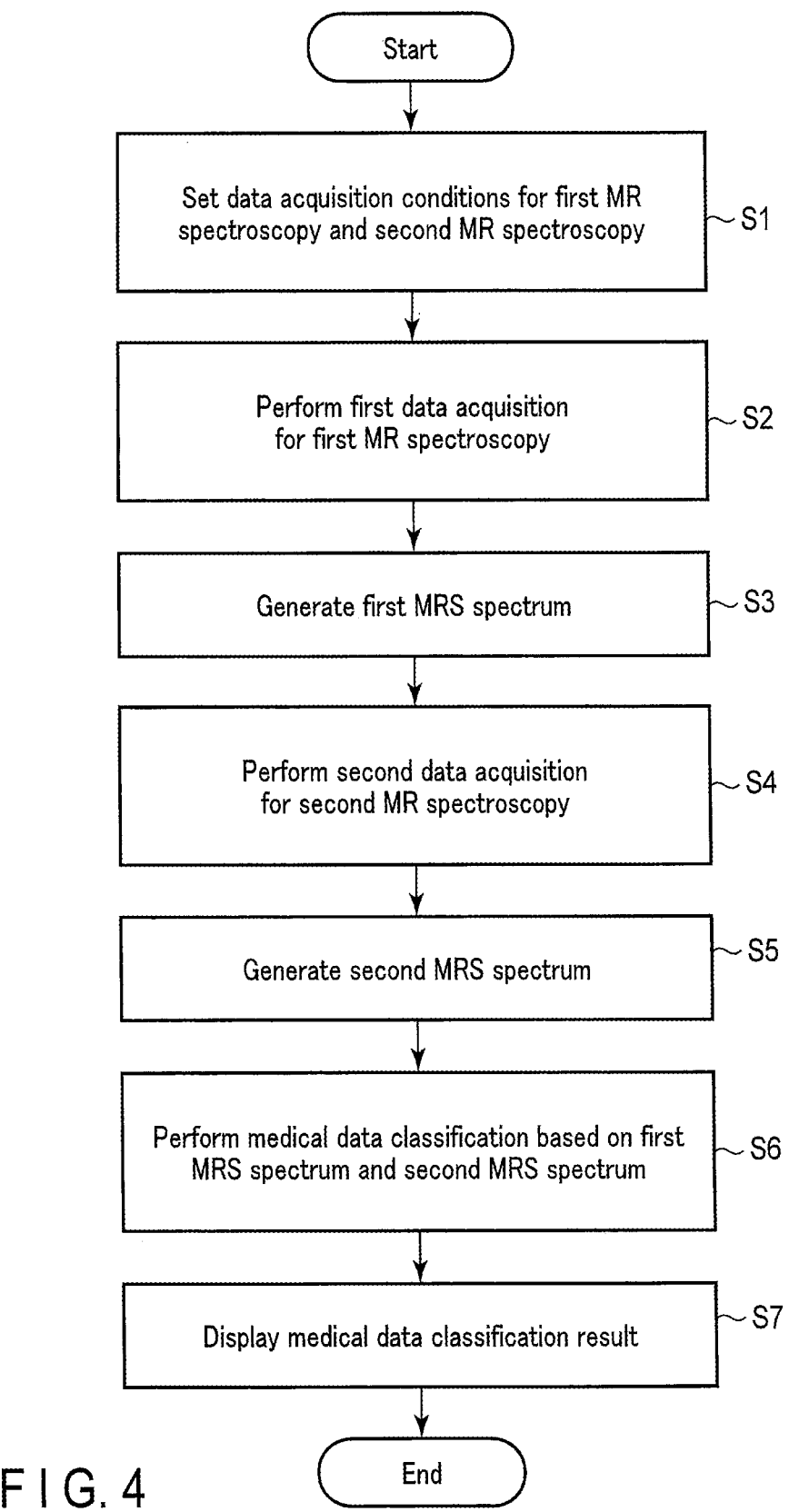
FIG. 4 is a diagram showing an example of a medical data classification process by a magnetic resonance imaging apparatus according to Example 1 of the first embodiment.

FIG. 4 is a diagram showing an example of a medical data classification process by a magnetic resonance imaging apparatus 1 according to Example 1 of the first embodiment.

As shown in FIG. 4, the processing circuitry 51 sets, through the realization of the condition setting function 512, the data acquisition conditions for the first MR spectroscopy and the second MR spectroscopy (step S1). The data acquisition conditions for MR spectroscopy include items such as pulse sequence, repeat time (TR), echo time (TE), number of times of integration, spectrum width, number of times of sampling, data acquisition method, and suppression pulse, etc. As a pulse sequence, for example PRESS (point resolved spectroscopy) and STEAM (stimulated echo acquisition mode), etc. are known. As for a TR, it is preferable that a long TR be set at 5000 ms or longer and a short TR be set at around 1000 ms to 3000 ms, for example. The longer the TR, the closer an obtained MR signal strength value comes to a true value, but the longer the data acquisition time. As for a TE, it is preferable that a long TE be set to around 100 ms to 300 ms and a short TE be set to around 20 ms to 100 ms. With a shorter TE, the number of observed peaks increases and the accuracy of the MRS spectrum is improved; with a longer TE, the number of observed peaks decreases and the visibility of the MRS spectrum is improved.

It suffices that the number of times of integration is set to 1 or greater. The number of spectrum widths and the number of times of sampling are condition items relating to a spectrum resolution. It suffices that the number of spectrum widths and the number of times of sampling are set at discretionary values. As a data acquisition method, a single voxel method for obtaining an MRS spectrum of a single voxel and a multiple voxel method for obtaining an MRS spectrum of each of multiple voxels are known. The suppression pulses applied during MR spectroscopy are, for example, a water suppression pulse and a fat suppression pulse. As data acquisition conditions, whether or not a water suppression pulse and a fat suppression pulse is to be applied and an application strength value of each suppression pulse are set. In Example 1, assume that both a water suppression pulse and a fat suppression pulse are applied.

In step S1, the processing circuitry 51 sets discretionary condition items of the data acquisition conditions for the first MR spectroscopy (hereinafter "first data acquisition conditions") and those of the data acquisition conditions for the second MR spectroscopy (hereinafter "second data acquisition conditions") at different values. In Example 1, the processing circuitry 51 sets condition values in such a manner that the combination of the condition items "TE" and "TR" differ between the first data acquisition conditions and the second data acquisition conditions. Among the first data acquisition conditions and the second data acquisition conditions, the condition values of both "TE" and "TR" may differ, only the condition value of "TE" may differ, or only the condition value of "TR" may differ. Although it is not necessary to set the other condition items, such as pulse sequence, the number of times of integration, spectrum width, the number of times of sampling, and a data acquisition method, etc., to the same values, assume that they are set to the same values for simplicity of descriptions.

Assume that a voxel targeted for data acquisition (hereinafter "voxel of interest") is set in a tumor area in the head of the subject P. As long as it is set in the tumor area, the voxel of interest may be set at either the same position or different positions for the first MR spectroscopy and the second MR spectroscopy. In Example 1, the data acquisition methods in the first MR spectroscopy and the second MR spectroscopy are a single voxel method, and the voxel of interest is therefore set at the same position for the first MR spectroscopy and the second MR spectroscopy.

After step S1, the sequence control circuitry 29 performs a first data acquisition for the first MR spectroscopy in accordance with the data acquisition conditions set in step S1 (step S2). By performing a pulse sequence for the first MR spectroscopy, a free induction decay (FID) signal or a spin echo signal is generated from the voxel of interest of the subject P. The receiver circuitry 25 receives an FID signal or a spin echo signal via the receiver coil 47, and processes the received FID signal or spin echo signal to collect k-space data relating to the voxel of interest. Assume the acquired k-space data is digital data in which an MR signal strength value transmitted from the voxel of interest is expressed as a time function. The pulse sequence for the first MR spectroscopy is repeated the number of times of integration, and k-space data corresponding to the number of times of integration is thereby acquired. Assume that k-space data is obtained by the processing circuitry 51 through the realization of the obtainment function 511.

After step S2, the processing circuitry 51 generates, by realization of the data processing function 513, a first MRS spectrum based on the k-space data obtained in step S2 (step S3). In step S3, for example, the processing circuitry 51 synthesizes the k-space data of the number of times of integration obtained in step S2, performs a Fourier transform on the synthesized k-space data, converts digital data in which the MR signal strength value is expressed as a frequency function, and performs post processing, such as phase correction or base line correction, on the converted digital data so as to generate a first MRS spectrum. The first MRS spectrum is stored in the memory 52.

After step S3, the sequence control circuitry 29 performs a second data acquisition for the second MR spectroscopy in accordance with the data acquisition conditions set in step S1 (step S4). In step S4, the receiver circuitry 25 collects k-space data of the number of times of integration for the voxel of interest. Assume that k-space data is obtained by the processing circuitry 51 through the realization of the obtainment function 511.

After step S4, the processing circuitry 51 generates, by realization of the data processing function 513, a second MRS spectrum based on the k-space data obtained in step S4 (step S5). In step S5, for example, the processing circuitry 51 synthesizes the k-space data of the number of times of integration obtained in step S4, performs a Fourier transform on the synthesized k-space data, converts digital data in which the MR signal strength value is expressed as a frequency function, and performs post processing, such as phase correction or base line correction, on the converted digital data so as to generate a second MRS spectrum. The second MRS spectrum is stored in the memory 52.

After step S5, the processing circuitry 51 performs medical data classification based on the first MRS spectrum generated in step S3 and the second MRS spectrum generated in step S5 (step S6). In step S6, the processing circuitry 51 performs medical data classification by applying the trained model to the first MRS spectrum and the second MRS spectrum.

Figure 5:
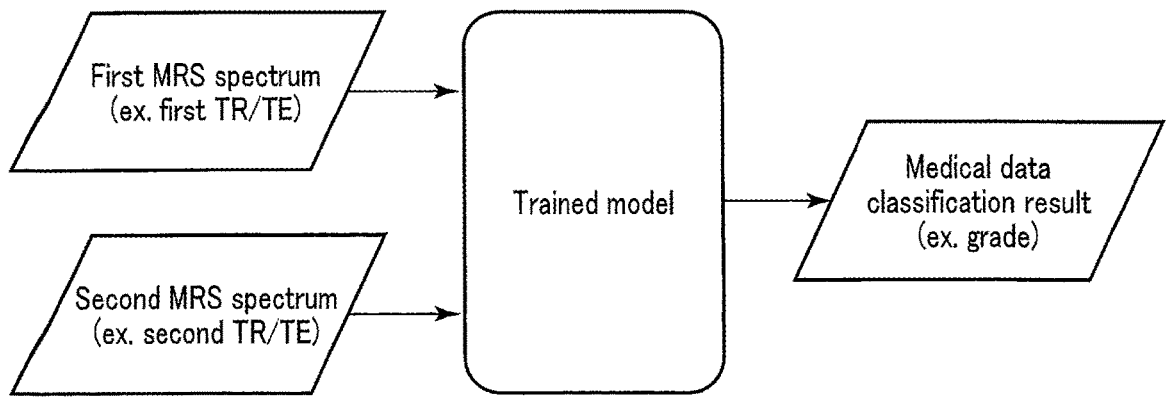
FIG. 5 is a diagram schematically showing an example of an input/output relationship of a trained model according to Example 1.

FIG. 5 is a diagram schematically showing an example of an input/output relationship of a trained model according to Example 1. As shown in FIG. 5, the trained model is a machine learning model into which a first MRS spectrum and a second MRS spectrum are input and in which parameters are learned so as to output a medical data classification result. The first MRS spectrum is acquired on the condition of first TR and TE as a combination, and the second MRS spectrum is acquired on the condition of second TR and TE as a combination. For example, the first MRS spectrum is set to TE=35 ms and TR=3000 ms, and the second MRS spectrum is set to TE=85 ms and TR=3000 ms, and the like. Of course, the TE may be the same and the TR may differ, or both the TE and the TR may differ between the first MRS spectrum and the second MRS spectrum. Thus, improvement in the accuracy of medical data classification is expected through using two MRS spectrums in which the combinations of TR and TE are different.

The first MRS spectrum and the second MRS spectrum that are input into the trained model are not limited to the waveform data of an MRS spectrum similar to the one shown in FIG. 3. For example, the MRS spectrum may be a combination of numerical value data of a chemical shift value and an MR signal strength (strength value) for each of the peaks in the MRS spectrum, or a combination of numerical value data of a chemical shift value and an MR signal strength value (strength value) and a width near a peak signal (FWHM: full width at half maximum). The MRS spectrum may be a combination of numerical value data of an identifier (name or symbol) of a metabolite of each of the peaks in the MRS spectrum and an MR signal strength value, or a combination of numerical value data of an identifier and an MR signal strength value and a peak width. The trained model may be any type of an intermediate obtained in the process of generating an MRS spectrum. For example, k-space data before summation is performed, k-space data after summation is performed, or k-space data after Fourier transform is performed may be input into the trained model. This MRS spectrum and the intermediate of the MRS spectrum are an example of MRS data acquired by MR spectroscopy.

After step S6, the processing circuitry 51 displays the medical data classification result that is output in step S6

(step S7). The medical data classification result is displayed on the display 53 with a predetermined layout.

Figure 6:
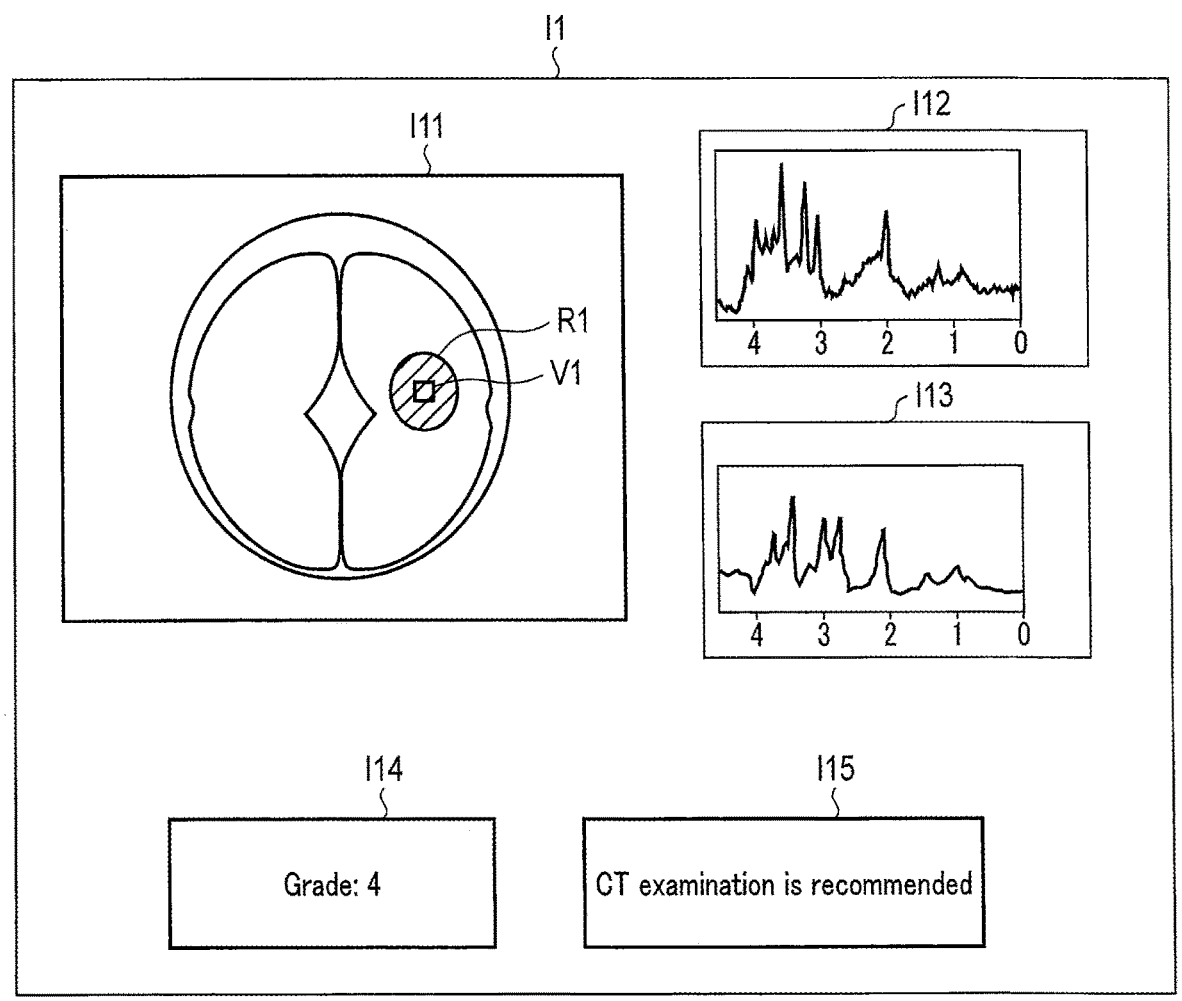
FIG. 6 shows an example of a display screen of a medical data classification result displayed in step S7 of FIG. 4.

FIG. 6 is a diagram showing an example of a display screen I1 for medical data classification results. As shown in FIG. 6, a voxel of interest setting image I11 is displayed on the display screen I1. A voxel of interest setting image I11 is an MR image in which voxels of interest V1 for the first MR spectroscopy and the second MR spectroscopy are set. In the voxel of interest setting image I11, a brain tumor region R1 is drawn, and in the brain tumor region R1, the voxels of interest V1 for the first MR spectroscopy and the second MR spectroscopy are drawn. If the voxel of interests of the first MR spectroscopy and the second MR spectroscopy are set at different positions, they will be drawn at different positions. The voxel of interest setting image I11 may be an MR image acquired by any imaging method.

As shown in FIG. 6, in the display screen I1, the first MRS spectrum I12 and the second MRS spectrum I13 provided for the medical data classification in step S6 are displayed. With the first MRS spectrum I12 and the second MRS spectrum I13 being displayed, a user can visually check the MRS spectrums provided to the medical data classification. In addition to the first MRS spectrum I12 and the second MRS spectrum I13, condition values for the data acquisition conditions, such as TR and TE, may also be displayed.

As shown in FIG. 6, a grade display section 114 is displayed in the display screen I1. In the grade display section 114, a grade as the medical data classification result that is output in step S6 is displayed. For example, "Grade: 4" is displayed as a grade of a brain tumor corresponding to the brain tumor region R1.

As shown in FIG. 6, a message display section 115 is displayed in the display screen I1. In the message display section 115, a message in accordance with the medical data classification result is displayed. For example, the processing circuitry 51 has a table in which medical data classification results and messages in accordance thereto are associated with each other, and extracts a message associated with a medical data classification result that is output in step S6 from the table, and causes the message display section 115 to display the extracted message. For example, if there are multiple values approximate to an output value of a grade determination and their ambiguity satisfies separately determined criteria, a message recommending a medical data classification diagnosis performed by a medical image diagnosis apparatus differing from the MRI apparatus 1 may be displayed in the message display section 115. For example, as shown in FIG. 6, a message such as "CT examination is recommended" may be displayed.

The description of the medical data classification processing according to Example 1 is completed.

The flow of the processing shown in FIG. 4 is merely an example and is not limited thereto. For example, the data acquisition conditions are set for the first MR spectroscopy and the second MR spectroscopy before the first MR spectroscopy and the second MR spectroscopy are performed in step S2, and it suffices that the data acquisition conditions for the second MR spectroscopy are performed before the second MR spectroscopy.

As in the above-described configuration, according to Example 1, grading is performed using the first MRS spectrum obtained through the first TR and TE and the second MRS spectrum obtained through the second TR and TE. Even for the same body part, it is possible to provide multiple spectrums having different SNRs (signal to noise ratios) to the trained model by changing the combination of TR and TE. By grading using such multiple MRS spectrums having different combinations of TR and TE, improvement in accuracy of grading can be expected.

Example 2

Figure 7:
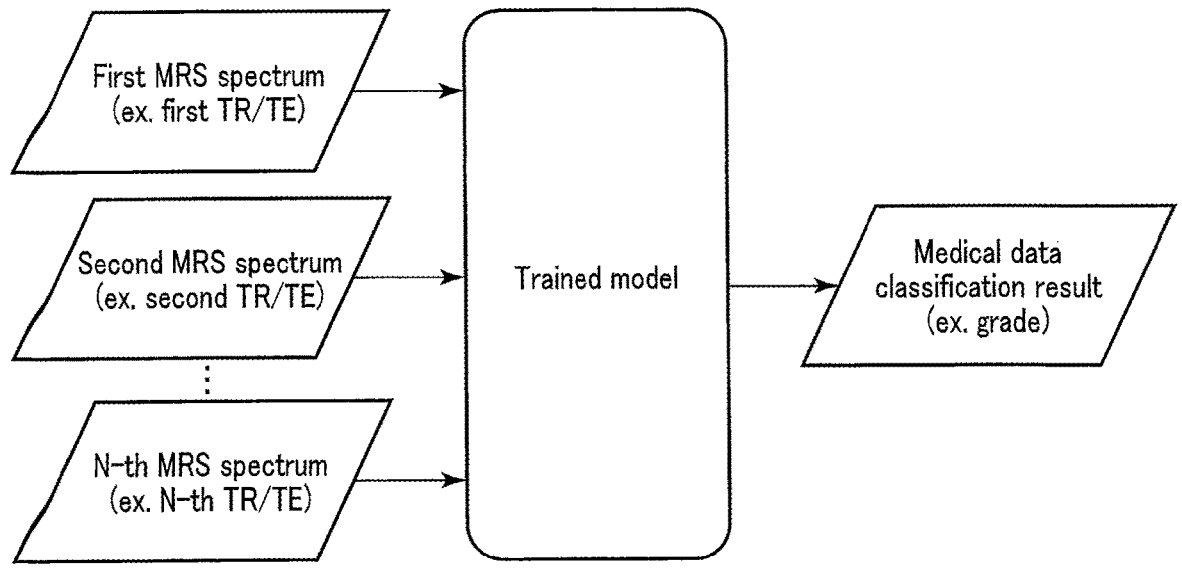
FIG. 7 is a diagram schematically showing an example of an input/output relationship of a trained model according to Example 2 of the first embodiment.

FIG. 7 is a diagram schematically showing an example of an input/output relationship of a trained model according to Example 2 of the first embodiment. As shown in FIG. 7, the trained model according to Example 2 is a machine learning model into which N MRS spectrums, from a first MRS spectrum to an Nth spectrum (N is an integer equal to or greater than 2), are input and in which parameters are learned so as to output a medical data classification result. N MRS spectrums are those obtained by data acquisition conditions in which TR and TE are different. For example, MRS spectrums acquired 2 to 1,000 times while changing TE every time may be input into the trained model. In this case, the TR may be the same or different.

By changing the data acquisition conditions, such as a combination of TR and TE, for a single area to acquire MRS spectrums multiple times, it is possible to acquire various types of MRS spectrums having different electro-magnetic environments for the region. It is expected that accuracy of the grading will be improved by giving these multiple MRS spectrums to the trained model.

Example 3

Figure 8:
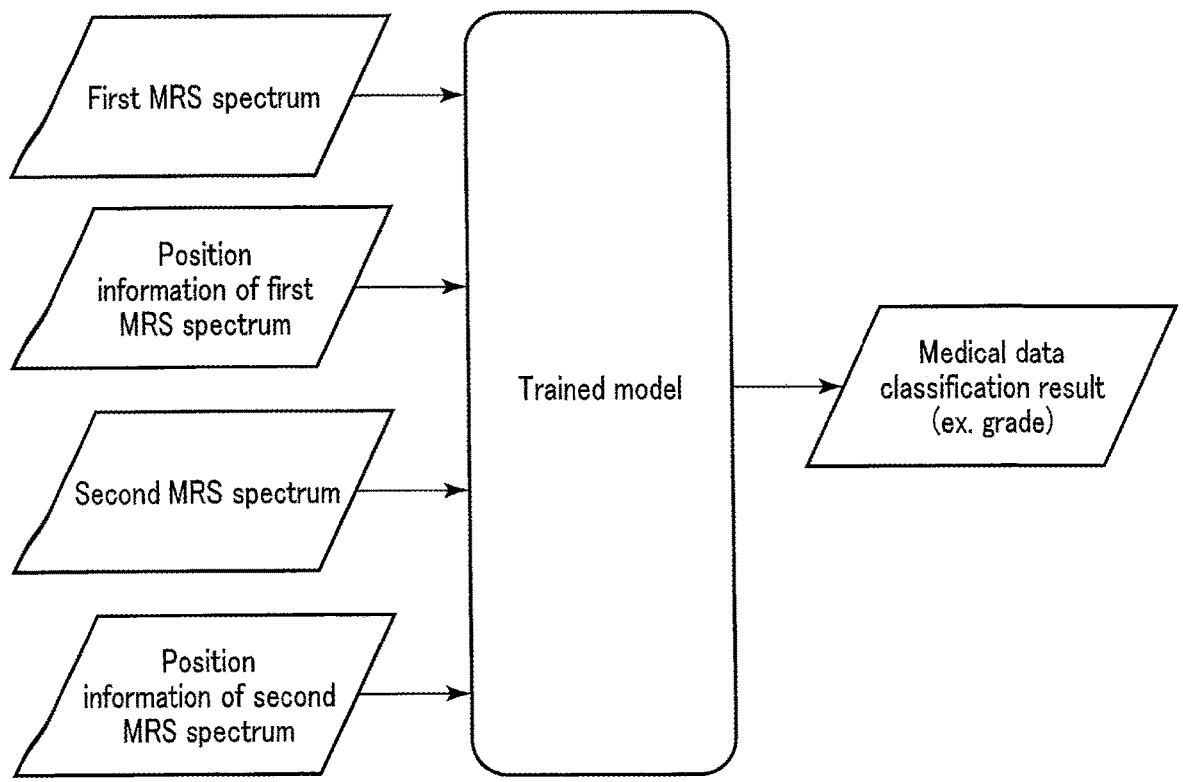
FIG. 8 is a diagram schematically showing an example of an input/output relationship of a trained model according to Example 3 of the first embodiment.

FIG. 8 is a diagram schematically showing an example of an input/output relationship of a trained model according to Example 3 of the first embodiment. As shown in FIG. 8, the trained model according to Example 3 is a machine learning model into which the first MRS spectrum and the position information thereof and the second MRS spectrum and the position information thereof are input and in which parameters are learned so as to output a medical data classification result. The position information of the first MRS spectrum is set to a coordinate of the voxel of interest of the first MR spectroscopy for acquiring this first MRS spectrum, and the position information of the second MRS spectrum is set to a coordinate of the voxel of interest of the second MR spectroscopy for acquiring this second MRS spectrum.

The position information of the first MRS spectrum and the position information of the second MRS spectrum may be determination factors in a medical data classification; thus, it is expected that accuracy of the grading is improved by giving these pieces of information to the trained model.

Example 4

FIG. 9 is a diagram schematically showing an example of an input/output relationship of a trained model according to Example 4 of the first embodiment. As shown in FIG. 9, the trained model according to Example 4 is a machine learning model into which a first MRS spectrum of a single voxel and a second MRS spectrum of a local area are input and in which parameters are learned so as to output a medical data classification result. The first MRS spectrum of a single voxel is an MRS spectrum relating to a voxel of interest acquired with a single voxel method. The second MRS spectrum of a local area is an MRS spectrum relating to a local area larger than a single voxel. A local area may be set to a discretionary size of, for example, 5×5 voxels, 9×9 voxels, or 13×13 voxels, etc. It is possible to perform MR spectroscopy on a local area with the PRESS method or the STEAM method, similarly to the single voxel method. It suffices that a local area is set so as to include a voxel of interest of the first MRS spectrum. A local area may be set so as not to include a voxel of interest of the first MRS spectrum.

An MR spectroscopy method adopted for a local area is not limited to a particular method. For example, the sequence control circuitry 29 may perform MR spectroscopy with the single voxel method on each of the plurality of voxels constituting a local area, or may perform chemical shift imaging on the voxels. The processing circuitry 51 may generate a plurality of MRS spectrums respectively corresponding to a plurality of voxels based on k-space data acquired by the MR spectroscopy through the single voxel method or by chemical shift imaging, generate a synthesized spectrum of the generated MRS spectrums, and input the synthesized spectrum into the trained model as a second MRS spectrum.

The MRS spectrum relating to a local area may be obtained by downsampling. For example, the sequence control circuitry 29 performs MR spectroscopy with the single voxel method or chemical shift imaging on each of a plurality voxels constituting a global area that includes a local area. The processing circuitry 51 generates a plurality of MRS spectrums respectively corresponding to the voxels constituting a global area based on k-space data acquired by the MR spectroscopy with the single voxel method or chemical shift imaging and performs downsampling, thereby generating a plurality of MRS spectrums respectively corresponding to the voxel constituting a local area. Thus, the MRS spectrums relating to a local area are generated.

The MRS spectrums relating to a local area may be obtained by masking. For example, the processing circuitry 51 generates a plurality of MRS spectrums respectively corresponding to voxels constituting a global area and performs masking on areas other than the local area, thereby generating MRS spectrums relating to the local area.

The second MRS spectrum of the local area has spectrum information in the proximity of a voxel of interest. It is expected that accuracy of the grading will be improved by giving these pieces of information to the trained model.

Example 5

FIG. 10 is a diagram schematically showing an example of an input/output relationship of a trained model according to Example 5 of the first embodiment. As shown in FIG. 10, the trained model according to Example 5 is a machine-learning model into which a first MRS spectrum by diffusion weighted MRS (MRS-diffusion) and a second MRS spectrum by diffusion weighted MRS are input and in which parameters are learned so as to output a medical data classification result. The diffusion weighted MRS is MR spectroscopy using a pulse sequence with a diffusion weighted gradient magnetic field (motion probing gradient, MPG). Data acquisition conditions are set in such a manner that a b-value, which is a strength of MPG, differs between the MR spectroscopy for acquiring a first MRS spectrum and the MR spectroscopy for acquiring a second MRS spectrum.

The MRS spectrum by the diffusion weighted MRS is an MRS spectrum in which diffusion of a hydrogen atomic nucleus in a metabolite is weighted by an application of MPG. It is expected that accuracy of the grading will be improved by giving these pieces of information relating to diffusion to the trained model.

Example 6

FIG. 11 is a diagram schematically showing an example of an input/output relationship of a trained model according to Example 6 of the first embodiment. As shown in FIG. 11, the trained model according to Example 6 is a machine learning model into which an MRS spectrum and an MR image in which parameters are learned are input so as to output a medical data classification result. The MR images are those acquired by T1 weighted imaging, T2 weighted imaging, T2* weighted imaging, MR angiography, diffusion weighted imaging, an inversion recovery method, etc., any applied method of these imaging methods, or other imaging. It suffices that the imaging area of MR imaging is set so as to include a voxel of interest of the MRS spectrum. Since MR spectroscopy and the MR imaging use different pulse sequences, the data acquisition conditions differ between MR spectroscopy and MR imaging.

Since the imaging area of MR imaging is set so as to include a voxel of interest of the MRS spectrum, an MR image includes information relating to an area in the vicinity of the voxel of interest of the MRS spectrum. Thus, it is expected that the accuracy of grading will be improved by performing grading with a use of an MR image in addition to MRS spectrums.

As an MR image, any type of MR image obtainable by the above-described MR imaging methods may be used. For example, as an MR image, an MRA image acquired by MR angiography can be used. The MRA image is an MR image in which blood flows are visualized. For example, if the MRA image includes a brain tumor area, blood flows flowing into or from a brain tumor are drawn; thus, it is expected that the accuracy of grading a brain tumor will be improved by providing such an MRA image to the trained model.

As an MR image, a FLAIR (fluid attenuated inversion recovery) image acquired with a FLAIR method, which is a type of inversion recovery method, may be used. The FLAIR method is an inversion recovery method in which an inversion time is set so as to cancel out a cerebrospinal fluid signal. Thus, the FLAIR image is a T1 weighted image in which cerebrospinal fluid signals are reduced. For example, since a brain tumor present in a brain sulcus or in perivascular spaces can be visualized in a FLAIR image, it is thus expected that the accuracy of grading a brain tumor will be improved through provision of such a FLAIR image to a trained model.

Besides the above-listed MR images, a T2 weighted image or a diffusion weighted image may be used. Furthermore, as an MR image to be input into the trained model, either image data of a whole MR image or image data of a local area or a point of interest in a whole MR image may be input. The local area is set so as to include a voxel of interest of an MRS spectrum, and a point of interest is set so as to correspond to a voxel of interest of an MRS spectrum. In this case, similarly to Example 3, position information of the local area or the point of interest may be input to the trained model, together with the position information of the local area or the point of interest. It is expected that accuracy of the grading will be improved by giving these pieces of position information to the trained model.

Example 7

FIG. 12 is a diagram schematically showing an example of an input/output relationship of a trained model according to Example 7 of the first embodiment. As shown in FIG. 12, the trained model according to Example 7 is a machine learning model into which a first MRS spectrum and a second MRS spectrum and medical data of other medical imaging are input and in which parameters are learned so as to output a medical data classification result. The first and second MRS spectrums are those obtained by data acquisition conditions in which combinations of TR and TE differ. The medical data of other medical imaging is medical data relating to a subject P acquired by a medical image diagnosis apparatus other than the MRI apparatus. As medical data acquired by another medical image diagnosis apparatus, medical images such as an X-ray CT image acquired by an X-ray computed tomography apparatus, an X-ray image acquired by an X-ray diagnosis apparatus, a nuclear medicine image acquired by a nuclear medicine diagnostic apparatus, an ultrasonic image acquired by an ultrasound diagnosis apparatus, and the like are applicable. An imaging area of the medical image is set so as to include voxels of interest of the first MRS spectrum and the second MRS spectrum. Medical data is not limited to a medical image; it may be raw data used for reconstruction of a medical image or a post-processed image generated by post processing of a medical image, such as analysis processing, etc.

The medical image of the other imaging includes information differing from information obtained by the MRI apparatus. For example, an X-ray CT image and an X-ray image include information relating to X-ray attenuation characteristics of a metabolite, a nuclear medicine image includes information relating to an amount of radioactive medicament accumulated in a metabolite, and an ultrasonic image includes information relating to ultrasound attenuation characteristics. It is expected that accuracy of the grading will be improved by providing these pieces of information to the trained model.

Example 8

FIG. 13 is a diagram schematically showing an example of an input/output relationship of a trained model according to Example 8 of the first embodiment. As shown in FIG. 13, the trained model according to Example 8 is a machine learning model into which a first MRS spectrum and a second MRS spectrum and medical data of a medical examination are input and in which parameters are learned so as to output a medical data classification result. The first and second MRS spectrums are those obtained by data acquisition conditions in which combinations TR and TE differ. As medical data for a medical examination, data such as examination values of various biochemical examination items relating to blood, urine, ascites fluid, and cerebrospinal fluid of a subject P may be used. Medical data for a medical examination may be data of an examination value of pathological examination items relating to a subject P or an NMR (nuclear magnetic resonance apparatus) spectrum obtained by an NMR.

The medical data of a medical examination includes information differing from information obtained by an MRI apparatus. It is expected that an accuracy of the grading will be improved by providing these pieces of information to the trained model.

Example 9

In Example 9, the first MRS spectrum and the second MRS spectrum are set in such a manner that their data acquisition conditions, except for a combination of TR and TE, differ therebetween.

For example, the first MRS spectrum and the second MRS spectrum are set in such a manner that application or non-application of a water suppression pulse and/or a fat suppression pulse differ therebetween. For example, the first MRS spectrum may be acquired by a pulse sequence that includes application of both a water suppression pulse and a fat suppression pulse, and the second MRS spectrum is acquired by a pulse sequence that does not include application of at least one of a water suppression pulse and a fat suppression pulse.

Specifically, if an MRS spectrum acquired by a pulse sequence that includes application of a water suppression pulse is used as the first MRS spectrum, an MRS spectrum acquired by a pulse sequence that does not include application of a water suppression pulse is used as the second MRS spectrum. It is thereby possible to provide information relating to free water suppressed in the first MRS spectrum to the trained model through the second MRS spectrum.

If an MRS spectrum acquired by a pulse sequence that includes application of a water suppression pulse is used as the first MRS spectrum, an MR image acquired by a pulse sequence that does not include a water suppression pulse may be used in place of the second MRS spectrum. Since a pulse sequence with a relatively long TE is used in MRS spectroscopy, it is preferable that the MR image acquired by a k-space trajectory capable of collecting MR signals with a short TE, for example an ultrashort TE (UTE) method or a short TE method, which are both a type of radial scanning method, be used. It is thereby possible to give information relating to a short TE to a trained model and it is expected that the accuracy of grading will thereby be improved.

Furthermore, the first MRS spectrum and the second MRS spectrum are set in such a manner that a combination of TR and TE also differs therebetween in addition to the application or non-application of a water suppression pulse and/or a fat suppression pulse. It is expected that the accuracy of grading will be improved by providing an MRS spectrum in which water and/or fat is not suppressed is provided to a trained model.

A different pulse sequence may be set for the first MRS spectrum and the second MRS spectrum. For example, it suffices that the first MRS spectrum is acquired with a pulse sequence of PRESS and the second MRS spectrum is acquired with a pulse sequence of STEAM. Furthermore, the data acquisition conditions may be set in such a manner that a combination of TR and TE in addition to a pulse sequence may differ between the first MRS spectrum and the second MRS spectrum. The pulse sequence affects area selectivity, TE, and MR signal strength. Therefore, it is expected that the accuracy of grading will be improved by applying the first MRS spectrum and the second MRS spectrum acquired through different pulse sequences to a trained model.

In Example 2, N MRS spectrums (N is an integer equal to or greater than 2, for example N is a number between 2 and 1000) having different TEs are input into a trained model; however, N sets of k-space data respectively corresponding to N echo signals having different TEs, which are obtained by multi-echo acquisition without a re-convergence pulse, may be input into a trained model, instead of N MRS spectrums. It is thereby possible to provide information relating to various TEs to a trained model, and it is thus expected that the accuracy of grading will be improved.

Example 10

FIG. 14 is a diagram schematically showing an example of an input/output relationship of a trained model according to Example 10 of the first embodiment. As shown in FIG. 14, the trained model according to Example 10 is a machine learning model into which an MRS spectrum, a FLAIR image, and a T2 weighted image are input and in which parameters are learned so as to output a presence/absence of an isocitrate dehydrogenase-1 (IDH1) mutation. A presence/absence of the IDH1 mutation is a type of medical data classification information.

It is known that a mutation of IDH1 produces 2-HG (2-hydroxyglutarate) (for example, Jelena Lazovic, et al., "Detection of 2-hydroxyglutaric acid in vivo by proton magnetic resonance spectroscopy in U87 glioma cells overexpressing isocitrate dehydrogenase-1 mutation", Neuro-Oncology 14(12): 1465-1472, 2012). In other words, there is a correlational relationship between the presence of 2-HG and a mutation of IDH1.

2-HG is detectable by MR spectroscopy and may form a peak in an MRS spectrum. 2-HG can be drawn in an MR morphological image, such as a FLAIR image and a T2 weighted image, etc.

The processing circuitry 51 inputs an MRS spectrum, a FLAIR image, and a T2-weighted image into a trained model. If for example an MR signal relating to 2-HG is included in at least one of the MRS spectrum, the FLAIR image, or the T2 weighted image, classification information indicating that the IDH1 mutation is present is output from the trained model. If for example an MR signal relating to 2-HG is not included in any of the MRS spectrum, the FLAIR image, or the T2 weighted image, classification information indicating that the IDH1 mutation is not present is output from the not yet trained model.

Example 10 can be combined with the foregoing Examples 1 to 9. As an example, a FLAIR image and a T2 weighted image are not input but 2 or more MRS spectrums set with different data acquisition conditions may be input. As another example, either one of a FLAIR image or a T2 weighted image, not both of them, may be input into a trained model. As another example, an MR morphological image that is input into a trained model along with an MRS spectrum is not limited to a FLAIR image or the T2 weighted image, and it may be an image capable of drawing 2-HG, such as a T1 weighed image and a proton density emphasis image, etc. As another example, an image that is input into a trained model along with an MRS spectrum is not limited to an image generated by an MRI apparatus and may be an image generated by a medical image diagnosis apparatus capable of drawing 2-HG, such as an image generated by an X-ray computer tomography apparatus or a nuclear medicine diagnostic apparatus. The trained model outputs a presence/absence of an IDH1 mutation; however, a 3- or more level grade expressing the degree of the IDH1 mutation may be output.

As described above, as an example, the processing circuitry 51 according to Example 10 either determines whether or not the IDH1 mutation is present in a subject or classifies the grade of the IDH1 mutation present in a subject, based on an MRS spectrum and an MR morphological image. According to Example 10, it is possible to classify a presence/absence of the IDH1 mutation and a grade with good accuracy through taking an MR morphological image that may draw 2-HG into consideration in addition to the MRS spectrums.

Example 11

The constituent elements described in the foregoing Examples 1 through 10 can be combined discretionarily to the extent that the examples do not depart from the spirit of the invention intended to provide more sets of medical information to a trained model compared to a single MRS spectrum.

[Review]

According to the forgoing examples of the first embodiment, the MRI apparatus 1 includes sequence control circuitry 29 and processing circuitry 51. The sequence control circuitry 29 performs, on the same subject P, a first data acquisition for chemical shift measurement and a second data acquisition for either chemical shift measurement or MR imaging, which differs from chemical shift measurement, on the same subject under certain conditions that differ between those data acquisitions. The processing circuitry 51 performs medical data classification on the subject based on first MR data obtained through the P first data acquisition and second MR data obtained through the second data acquisition.

According to the above configuration, the processing circuitry 51 performs medical data classification based on not only the first MR data but also the second MR data. Since the second MR data includes information that cannot be obtained by the first MR data, it is thus expected that the accuracy of grading will be improved by performing medical data classification based on not only the first MR data but also the second MR data.

Second Embodiment

Hereinafter, the medical data processing apparatus 2 according to the second embodiments will be described. Note that in the following description, the same reference numerals denote constituent elements having almost the same functions as those included in the first embodiment, and a repeat description will be made only when required.

FIG. 15 is a diagram showing a configuration example of the medical data processing apparatus 2 according to the second embodiment. As shown in FIG. 15, the medical data processing apparatus 2 is a computer having a processing circuitry 51, a memory 52, a display 53, an input interface 54, and a communication interface 55. The processing circuitry 51 executes various types of programs to implement an obtainment function 511, a data processing function 513, a classification function 514, and a display control function 515. Assume that the medical data processing apparatus 2 is a workstation included in a PACS (picture archiving and communication system) or capable of accessing the PACS, not a computer implemented in an MRI apparatus.

As shown in FIG. 15, the configuration and functions of the medical data processing apparatus 2 are approximately the same as those of the host computer 50 of the MRI apparatus 1 according to the first embodiment.

The processing circuitry 51 according to the second embodiment performs medical data classification on the same subject based on first medical data of chemical shift measurement and second medical data of chemical shift measurement or a medical examination differing from the chemical shift measurement, both obtained under different data acquisition conditions from the same subject. The first medical data and the second medical data are obtained from a PACS server, etc. by the processing circuitry 51 via the communication interface 55. The first medical data and the second medical data may be the same medical data relating to a same examination on a subject P or medical data relating to different examinations. For example, the second medical data may be medical data of a past examination with respect to an examination for the first medical data (current examination). The processing circuitry 51 applies the first medical data and the second medical data to a trained model and outputs a medical data classification result.

FIG. 16 is a diagram schematically showing an example of an input/output relationship of a trained model according to the second embodiment. As shown in FIG. 16, the trained model according to the second embodiment is a machine learning model into which first medical data of chemical shift measurement and second medical data of either chemical shift measurement or a medical examination differing from the chemical shift measurement are input and in which parameters are learned so as to output a medical data classification result. The first medical data and the second medical data are medical data acquired under different data acquisition conditions. As the trained model or the machine learning model according to the second embodiment, a classifier or an identifier, such as a neural network, deep neural network, support vector machine, or random forest, etc., is used, similarly to the first embodiment. The medical data classification result is information indicating a result of medical data classification of first medical data and second medical data regarding a subject. A medical data classification result is for example a grade of a disease by which a subject is being affected and a presence/absence of IDH1 mutation, similarly to the first embodiment.

The first medical data of chemical shift measurement is MR data of chemical shift measurement obtained by the MRI apparatus, similar to the first MR data in the first embodiment. Chemical shift measurement is applicable to MR spectroscopy, chemical shift imaging, CEST, or ZAPPED, similarly to the first embodiment.

Two sets of medical data obtained by chemical shift measurement are MR data of chemical shift measurement obtained by an MRI apparatus, similarly to the second MR data in the first embodiment. Two sets of medical data obtained by a medical examination differing from chemical shift measurement is applicable to an MR image obtained by MR imaging, a medical image obtained by other medical imaging, or an examination result obtained by a medical examination, similarly to the first embodiment.

A trained model according to the second embodiment is generated by a model learning apparatus. The model learning apparatus generates a trained model by having a machine learning model conduct machine learning based on multiple training samples. Training samples are combinations of first medical data and second medical data, which are input data, and a medical data classification result as correct answer data ("correct answer medical data classification result"). The model learning apparatus applies a machine learning model to the first medical data and the second medical data and performs a forward propagation process, and outputs a deduced medical data classification result. Next, the model learning apparatus performs backpropagation by applying a difference (error) between the estimated classification result and the correct classification result to the machine learning model, and calculates a gradient vector, which is a derivative of an error function which is a parameter function. Subsequently, the model learning apparatus updates parameters of the machine learning model based on a gradient vector. These forward propagation processing, backpropagation processing, and parameter updating processing are repeated while changing the training samples, and a parameter that minimizes an error function is determined in accordance with a predetermined optimization method. A trained model is thus generated. The generated trained model is stored in the memory 52 of the medical data processing apparatus 2.

According to the second embodiment, even if a measurement mechanism for chemical shift measurement is not provided, it is possible to perform grading using chemical shift measurement. According to the second embodiment, it is possible to acquire second medical data acquired by various types of medical image diagnosis apparatuses; therefore, it is possible to improve the accuracy of grading by providing such medical data to a trained model together with first medical data obtained by chemical shift measurement.

According to at least one of the foregoing embodiments, it is possible to improve an accuracy of medical data classification using chemical shift measurement.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes its function by reading and executing the program stored in the storage circuitry. The program may be directly incorporated into the circuit of the processor instead of being stored in the storage circuit. In this case, the processor implements the function by reading and executing the program incorporated into the circuit. The function corresponding to the program may be realized by a combination of logic circuits, not by executing the program. Each processor of the present embodiment is not limited to a case where each processor is configured as a single circuit; a plurality of independent circuits may be combined into one processor to realize the function of the processor. Furthermore, a plurality of constituent elements shown in FIGS. 1 and 16 may be integrated into one processor to implement the functions.

While certain embodiments have been described, these embodiments have been presented by way of example only, and are not intended to limit the scope of the inventions. Indeed, the embodiments described herein may be embodied in a variety of other forms; furthermore, various omissions, substitutions, changes, and combinations of embodiments in the form of the embodiment described herein may be made without departing from the spirit of the invention. The accompanying claims and their equivalents are intended to cover such forms or modifications as would fall within the scope and spirit of the invention.

The invention claimed is:

1. A medical image processing apparatus, comprising:
processing circuitry configured to perform medical data classification on a same subject based on first medical data obtained through chemical shift measurement and second medical data obtained through the chemical shift measurement or a medical examination differing from the chemical shift measurement, the first and second medical data being obtained under different data acquisition conditions for the same subject, wherein
in the first data acquisition, first MR spectroscopy regarding a first TR and/or TE is performed as the chemical shift measurement,
the first MR data is MR data obtained by the first MR spectroscopy that includes application of a water suppression pulse and/or application of a fat suppression pulse,
the second data acquisition performs second MR spectroscopy on second TR and/or TE differing from the first TR and/or TE as the chemical shift measurement, and
the second MR data is MR data obtained by the second MR spectroscopy that does not include application of the water suppression pulse and/or application of the fat suppression pulse.

2. A magnetic resonance imaging apparatus, comprising:
sequence control circuitry configured to perform, on a same subject, a first data acquisition for chemical shift measurement and a second data acquisition for chemical shift measurement or MR imaging differing from the chemical shift measurement, data acquisition conditions of the first data acquisition being different from those of the second data acquisition; and
processing circuitry configured to perform medical data classification regarding the subject based on first MR data obtained by the first data acquisition and second MR data obtained by the second data acquisition, wherein
in the first data acquisition, first MR spectroscopy regarding a first TR and/or TE is performed as the chemical shift measurement,
the first MR data is MR data obtained by the first MR spectroscopy that includes application of a water suppression pulse and/or application of a fat suppression pulse,
the second data acquisition performs second MR spectroscopy on second TR and/or TE differing from the first TR and/or TE as the chemical shift measurement, and
the second MR data is MR data obtained by the second MR spectroscopy that does not include application of the water suppression pulse and/or application of the fat suppression pulse.

3. The magnetic resonance imaging apparatus according to claim 2, wherein
the first MR data is data relating to a single voxel, and
the second MR data is data relating to a local area.

4. The magnetic resonance imaging apparatus according to claim 2, wherein the first MR data and the second MR data are MRS data obtained by diffusion weighted MR spectroscopy.

5. The magnetic resonance imaging apparatus according to claim 2, wherein the second data acquisition is data acquisition for MR angiography or FLAIR as the MR imaging.

6. The magnetic resonance imaging apparatus according to claim 2, wherein the chemical shift measurement is MR spectroscopy, chemical shift imaging, chemical exchange spectroscopy (CEST), or z-spectrum analysis providing proton environment data (ZAPPED).

7. The magnetic resonance imaging apparatus according to claim 2, wherein the processing circuitry is further configured to perform medical data classification regarding the subject based on the first MR data and the second MR data, and medical data acquired by other medical examinations differing from chemical shift measurement and magnetic resonance imaging.

8. The magnetic resonance imaging apparatus according to claim 2, wherein the processing circuitry is further configured to output, as the medical data classification, a grade of a disease that the subject is affected by.

9. The magnetic resonance imaging apparatus according to claim 2, wherein the processing circuitry is further configured to perform the medical data classification by applying the first MR data and the second MR data to a trained model.

10. The magnetic resonance imaging apparatus according to claim 2, wherein the processing circuitry is further configured to cause a display device to display a result of the medical data classification.

11. The magnetic resonance imaging apparatus according to claim 10, wherein the processing circuitry is further configured to cause the display device to display a message recommending a medical image diagnosis by another medical image diagnosis apparatus in accordance with the result.

12. The magnetic resonance imaging apparatus according to claim 2, wherein the processing circuitry is further configured to perform the medical data classification based on the first MR data, the second MR data, position information of the first MR data, and position information of the second MR data.

13. The magnetic resonance imaging apparatus according to claim 2, wherein
the first MR data is data relating to a first area set in the subject, and
the second MR data is data relating to a second area set in the subject, the second area being larger than the first area.

14. The magnetic resonance imaging apparatus according to claim 2, wherein
the first MR data is an MRS spectrum,
the second MR data is an MR morphological image, and
the processing circuitry is further configured to perform classification of a presence/absence of an IDH1 mutation in the subject or a grade of an IDH1 mutation present in the subject, based on the MRS spectrum and the MR morphological image.

15. The magnetic resonance imaging apparatus according to claim 14, wherein the MR morphological image includes a FLAIR image and a T2 weighted image.

16. The magnetic resonance imaging apparatus according to claim 14, wherein the processing circuitry is further configured to apply the MRS spectrum and the MR morphological image to a trained model and perform classification of a presence/absence of an IDH1 mutation in the subject or a grade of an IDH1 mutation present in the subject, based on the MRS spectrum and the MR morphological image.

* * * * *